US007897171B2

(12) United States Patent
Strickler et al.

(10) Patent No.: US 7,897,171 B2
(45) Date of Patent: Mar. 1, 2011

(54) MEDICAL DEVICES HAVING IMPROVED MECHANICAL PERFORMANCE

(75) Inventors: Frederick H. Strickler, Natick, MA (US); Mark Boden, Harrisville, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/395,276

(22) Filed: Feb. 27, 2009

(65) Prior Publication Data
US 2009/0186067 A1 Jul. 23, 2009

Related U.S. Application Data

(63) Continuation-in-part of application No. 11/809,459, filed on Jun. 1, 2007.

(60) Provisional application No. 60/840,309, filed on Aug. 25, 2006.

(51) Int. Cl.
*A61F 13/00* (2006.01)

(52) U.S. Cl. .................. 424/443; 424/422; 424/423; 424/486; 525/199; 525/222; 525/227; 525/276; 525/298; 525/302; 525/308

(58) Field of Classification Search .................. 525/166, 525/199, 222, 227, 276, 298, 302, 308; 424/422, 424/423, 424, 425, 426, 443, 486
See application file for complete search history.

(56) References Cited

U.S. PATENT DOCUMENTS

| 3,933,747 | A | * | 1/1976 | Nowak et al. ............... 525/340 |
| 4,036,719 | A |   | 7/1977 | Lyons |
| 5,491,193 | A |   | 2/1996 | Erickson |
| 5,741,331 | A | * | 4/1998 | Pinchuk ...................... 424/423 |
| 5,981,785 | A |   | 11/1999 | Faust et al. |
| 6,051,657 | A |   | 4/2000 | Faust et al. |
| 6,194,597 | B1 |   | 2/2001 | Faust et al. |
| 6,268,451 | B1 | * | 7/2001 | Faust et al. ................. 526/279 |
| 6,469,115 | B1 |   | 10/2002 | Faust et al. |
| 6,471,955 | B1 |   | 10/2002 | Tremont et al. |
| 6,750,267 | B2 |   | 6/2004 | Faust et al. |
| 6,765,059 | B2 |   | 7/2004 | Corley |
| 6,887,270 | B2 | * | 5/2005 | Miller et al. .............. 623/11.11 |
| 2004/0202691 | A1 |   | 10/2004 | Richard |
| 2004/0208841 | A1 |   | 10/2004 | Salovey et al. |
| 2005/0025801 | A1 |   | 2/2005 | Richard et al. |
| 2005/0031813 | A1 |   | 2/2005 | Conrnette et al. |
| 2005/0064011 | A1 | * | 3/2005 | Song et al. ................. 424/423 |
| 2005/0218551 | A1 |   | 10/2005 | Halahmi et al. |
| 2006/0013853 | A1 |   | 1/2006 | Richard |
| 2008/0051541 | A1 |   | 2/2008 | Strickler et al. |

FOREIGN PATENT DOCUMENTS

| WO | 2006014607 | 2/2006 |
| WO | 2006083904 | 8/2006 |
| WO | 2007-143159 | 12/2007 |
| WO | 2008027107 | 3/2008 |

OTHER PUBLICATIONS

Sipos, L.; Som, A.; Faust, R.; Richard, R.; Schwarz, M.; Ranade, S.; Boden, M.; Chan, K.; Biomacromolecules, 2005, 6, 2570-2582.*
Sakurai, S.; Aida, S.; Nomura, S.; Polymer, 1999, 40, 2071-2076.*
Odian, G.; Principles of Polymerization, 2004, 521.*
Cho, J.C.; Cheng, G.; Feng, D.; Faust, R.; Biomacromolecules, 2006, 7, 2997-3007.*
Shi, Z.; Holdcroft, S.; Macromolecules, 37(6), 2004, p. 2084-2089.*
S. Sakurai, et al., "Mechanical Properties of Polystyrene-Block-Polybutadiene-Block-Polystyrene Triblock Copolymers Crosslinked in the Disordered State," Polymer, 40(1999), pp. 2071-2076.
C. Decker, et al., "High-Speed Photocrosslinking of Thermoplastic Styrene-Butadiene Elastomers," Journal of Applied Polymer Science, 2000, vol. 77, Issue 9, pp. 1902-1912.
Decker, etal., "Photocrosslinking of Functionalized Rubbers, $7^a$ Styrene-Butadiene Block Copolymers," Macromolecular Chemistry and Physics, 1999, vol. 200, Issue 2, pp. 358-367.
P. Bracco, et al., "Radiation-Induced Crosslinking of UHMWPE in the Presence of Co-Agents: Chemical and Mechanical Characterization," Polymer, 46(2005), pp. 10648-10657.
H. Kanbara, et al., "Measurement of Crosslinking Degree for Electron Beam Irradiated Block Copolymers," Polymer Engineering and Science, Apr. 2004, vol. 34, Issue 8, pp. 691-694.
S.M. Kurtz et al., "Advances in the Processing, Sterilization, and Crosslinking of Ultra-High Molecular Weight Polyethylene for Total Joint Arthroplasty," Biomaterials, 20(1999), pp. 1659-1688.
S. Itsuno et al., "Novel Method for Halomethylation of Cross-linked Polystyrenes," J. Am. Chem. Soc. 1990, 112, pp. 8187-8188.
Y. Sakai et al., "Humidity Sensor Durable at High Humidity using Simultaneously Crosslinked and Quaternized Poly (chloromethyl styrene)," Sensors and Actuators B: Chemical 25(1-3), 1995, pp. 689-691.
T. Hiashihara et al., "Grafting of Poly(Dimethylsiloxane) Onto Poly(Styrene-Block-lsobutylene-Block-Styrene)," Polymer Pre-Prints, 2007, 48(2), 1037-1038.
International Search Report and Written Opinion for related International Application PCT/US2007/018840.
Senake Perera, "Radiation Degradation of Expoxidized Natural Rubber Studied by Solid-State Nuclear Magnetic Resonance and Infrared Spectroscopy," Polymer Int. 49 (2000) 691-698.
Basheer et al., "The Radiation Crosslinking of Block Copolymers of Butadiene and Styrene," Die Makromolekulare Chemie 183 (2003) 2141-2151.
Lewis, "Properties of Crosslinked Ultra-High-Molecular-Weight Polyethylene," Biomaterials 22 (2001) 371-401.
Hemmerich, "Radiation Sterilization Polymer Materials Selection for Radiation-Sterilized Products," Medical Device & Diagnostic Industry Magazine, Feb. 2000, 4 pages, downloaded May 8, 2006. http://www.devicelink.com/mddi/archive/00/02/006.html.

* cited by examiner

*Primary Examiner*—David Wu
*Assistant Examiner*—Robert Jones
(74) *Attorney, Agent, or Firm*—Mayer & Williams PC; David B. Bonham; Keum J. Park

(57) ABSTRACT

According to an aspect of the present invention, implantable or insertable medical devices are provided that contain at least one covalently crosslinked polymeric region, which contains at least one block copolymer comprising at least one low Tg block and at least one high Tg block.

28 Claims, No Drawings

MEDICAL DEVICES HAVING IMPROVED MECHANICAL PERFORMANCE

STATEMENT OF RELATED APPLICATION

This application is a continuation-in-part of co-pending U.S. patent application Ser. No. 11/809,459, filed Jun. 1, 2007, which claims the benefit of U.S. Provisional Patent Application Ser. No. 60/840,309, filed Aug. 25, 2006, each of which is hereby incorporated by reference in its entirety.

FIELD OF THE INVENTION

The present invention relates generally to medical devices, and more particularly to implantable or insertable medical devices.

BACKGROUND OF THE INVENTION

Thermoplastic elastomers are elastomeric (i.e., reversibly deformable) polymers that form physical crosslinks which are reversible, for example, by dissolving or melting the polymer. Triblock copolymers having an elastomeric low glass transition temperature (Tg) midblock and hard elevated Tg endblocks are common examples of thermoplastic elastomers. As is well known, such copolymers tend to phase separate, with the elastomeric blocks aggregating to form elastomeric phase domains and the hard blocks aggregating to form hard phase domains. Without wishing to be bound by theory, it is believed that because each elastomeric block has a hard block at each end, and because different hard blocks within the same triblock copolymer are capable of occupying two different hard phase domains, the hard phase domains become physically crosslinked to one another via the soft blocks.

Examples of such triblock copolymers are poly(styrene-b-isoprene-b-styrene) (SIS), poly(styrene-b-butadiene-b-polystyrene) (SBS), poly(styrene-b-ethylene/butylene-b-styrene) (SEBS), and poly(styrene-b-isobutylene-b-styrene) (SIBS). Taking SIBS as a specific example, these polymers have proven valuable as drug release polymers in implantable or insertable drug-releasing medical devices such as drug-eluting coronary stents. In addition to their drug release characteristics, SIBS copolymers have been shown to have excellent biostability and biocompatibility, particularly within the vasculature. Moreover, they have excellent mechanical properties for coronary stent applications, including good elasticity and high tensile strength. As a result of their mechanical properties, these polymers are able to undergo crimping and to expand as the stent is expanded.

Despite the desirable qualities of these and other thermoplastic elastomers, there are situations where it would be desirable to improve one or more mechanical properties of these materials, including, for example, one or more of strength, elongation at break, tear resistance, creep resistance, and abrasion resistance, among others.

SUMMARY OF THE INVENTION

According to an aspect of the present invention, implantable or insertable medical devices are provided that contain at least one covalently crosslinked polymeric region, which contains at least one block copolymer. The at least one block copolymer further contains at least one low Tg block and at least one high Tg block.

An advantage of the present invention is that that one or more mechanical properties of various multiblock thermoplastic elastomers may be improved for a given medical application.

These and other aspects, embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

According to an aspect of the present invention, implantable or insertable medical devices are provided that contain at least one covalently crosslinked polymeric region, which contains at least one block copolymer. The at least one block copolymer further contains at least one low Tg block and at least one high Tg block.

Medical devices benefiting from the present invention vary widely and include a variety of medical devices, which are implanted or inserted into a subject, either for procedural uses or as implants.

Examples of medical devices which may utilize covalently crosslinked polymeric regions in accordance with the invention include prosthetic devices, for example, load bearing joints, such as knee, hip, and spinal disk replacements. There is a general need to reduce oxidation and wear resistance in such implants as well.

Further examples of medical devices which may utilize covalently crosslinked polymeric regions in accordance with the invention include those requiring coatings that are wear resistant and have relatively low coefficients of friction. Such devices include those that transit and/or contact tissue such as needles, sutures, guidewires, catheters, balloons, and balloon catheters. In the specific example of a balloon, durable coatings with good wear resistance to tissue are highly desirable. Moreover, such coatings may also reduce withdrawal resistance when removing the balloon from dilated tissue or from a deployed stent, especially when using non-compliant balloons that do not fully deflate or balloons that have a tendency to creep after multiple inflation/deflation cycles (i.e., they do not deflate back to their original size). Such coatings could also allow balloons to re-cross stent lesions more easily. Such coatings could also increase the tear resistance and the abrasion resistance catheters.

Examples of medical devices which may utilize covalently crosslinked polymeric regions in accordance with the invention include stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts, etc.), vascular access ports, dialysis ports, catheters (e.g., urological catheters or vascular catheters such as balloon catheters and various central venous catheters), guide wires, balloons, filters (e.g. vena cava filters and mesh filters for distal protection devices), embolization devices including cerebral aneurysm filler coils (including Guglielmi detachable coils and metal coils), embolic agents, tissue bulking devices, septal defect closure devices, drug depots that are adapted for placement in an artery for treatment of the portion of the artery distal to the device, myocardial plugs, patches, leads including pacemaker leads, defibrillation leads and coils, neurostimulation leads such as spinal cord stimulation leads, deep brain stimulation leads, peripheral nerve stimulation leads, cochlear implant leads and retinal implant leads, pulse generators, ventricular assist devices including left ventricular assist hearts and pumps, total artificial hearts, shunts, valves including heart valves and vascular valves, anastomosis clips and rings, cochlear implants, tympanostomy tubes, thoracic drainage tubes, nephrostomy tubes, and tissue engineering scaffolds for cartilage, bone, skin, nerve (e.g., for neural pathway regeneration, including the spinal cord), and other in vivo tissue regeneration, sutures, suture anchors, tissue staples and ligating clips at surgical sites, cannulae, metal wire ligatures, urethral slings, hernia "meshes", artificial ligaments, tacks for ligament attachment and meniscal repair, joint prostheses, spinal discs and nuclei, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants and root sealer, whitening strips, belly bands, gastric balloons and obesity devices, contact lenses, interocular lenses, punctum plugs, glaucoma shunts, or other devices that are implanted or inserted into the body.

Hence, in some embodiments, the polymeric regions of the present invention correspond to an entire medical device. In other embodiments, the polymeric regions correspond to one or more portions of a medical device. For instance, the polymeric regions can be in the form of medical device components, in the form of one or more fibers which are incorporated into a medical device, in the form of one or more polymeric layers (e.g., coatings) formed over all or only a portion of an underlying substrate, and so forth. Materials for use as underlying medical device substrates include ceramic, metallic and polymeric substrates. The substrate material can also be a carbon- or silicon-based material, among others. Layers can be provided over an underlying substrate at a variety of locations and in a variety of shapes (e.g., in the form of a series of rectangles, stripes, or any other continuous or non-continuous pattern). As used herein a "layer" of a given material is a region of that material whose thickness is small compared to both its length and width. As used herein a layer need not be planar, for example, taking on the contours of an underlying substrate. Layers can be discontinuous (e.g., patterned).

As used herein, a "polymeric region" is a region (e.g., an entire device, a device component, a device coating layer, etc.) that contains polymers, for example, from 50 wt % or less to 75 wt % to 90 wt % to 95 wt % to 97.5 wt % to 99 wt % or more polymers.

As used herein, "polymers" are molecules containing multiple copies (e.g., from 2 to 5 to 10 to 25 to 50 to 100 to 250 to 500 to 1000 or more copies) of one or more constitutional units, commonly referred to as monomers.

Polymers may take on a number of configurations, which may be selected, for example, from cyclic, linear and branched configurations, among others. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ in composition, for instance, because a constitutional unit (i.e., a monomer) is found in one polymer block that is not found in another polymer block. As used herein, a "polymer block" is a grouping of constitutional units (e.g., 5 to 10 to 25 to 50 to 100 to 250 to 500 to 1000 or more units). Blocks can be branched or unbranched. Blocks can contain a single type of constitutional unit (also referred to herein as "homopolymeric blocks") or multiple types of constitutional units (also referred to herein as "copolymeric blocks") which may be present, for example, in a random, statistical, gradient, or periodic (e.g., alternating) distribution.

As used herein, a "chain" is a linear polymer or a portion thereof, for example, a linear block.

As used herein, a "low Tg polymer block" is one that displays a Tg that is below body temperature, more typically from 35° C. to 20° C. to 0° C. to −25° C. to −50° C. or below. Conversely, as used herein, an elevated or "high Tg polymer block" is one that displays a Tg that is above body temperature, more typically from 40° C. to 50° C. to 75° C. to 100° C. or above. Tg can be measured by differential scanning calorimetry (DSC).

Block copolymer configurations may vary widely and include, for example, the following configurations, among others, which comprise two more high Tg polymer chains (designated "H") and one or more low Tg polymer chains (designated "L"): (a) block copolymers having alternating chains of the type HLH, $(HL)_m$, $L(HL)_m$ and $H(LH)_m$ where m is a positive whole number of 2 or more, (b) multiarm (including star) copolymers such as $X(LH)_n$, where n is a positive whole number of 2 or more, and X is a hub species (e.g., an initiator molecule residue, a linking residue, etc.), and (c) comb copolymers having an L chain backbone and multiple H side chains.

Specific examples of low Tg polymer blocks include homopolymer and copolymer blocks containing one or more of the following (listed along with published Tg's for homopolymers of the same): (1) alkene monomers including ethylene, propylene (Tg −8 to −13° C.), isobutylene (Tg −73° C.), 1-butene (Tg −24° C.), 4-methyl pentene (Tg 29° C.), 1-octene (Tg −63° C.) and other α-olefins, dienes such as 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, and 3-butyl-1,3-octadiene; (2) acrylic monomers including: (a) alkyl acrylates such as methyl acrylate (Tg 10° C.), ethyl acrylate (Tg −24° C.), propyl acrylate, isopropyl acrylate (Tg −11° C., isotactic), butyl acrylate (Tg −54° C.), sec-butyl acrylate (Tg −26° C.), isobutyl acrylate (Tg −24° C.), cyclohexyl acrylate (Tg 19° C.), 2-ethylhexyl acrylate (Tg −50° C.), dodecyl acrylate (Tg −3° C.) and hexadecyl acrylate (Tg 35° C.), (b) arylalkyl acrylates such as benzyl acrylate (Tg 6° C.), (c) alkoxyalkyl acrylates such as 2-ethoxyethyl acrylate (Tg −50° C.) and 2-methoxyethyl acrylate (Tg −50° C.), (d) halo-alkyl acrylates (Tg −10° C.) and (e) cyano-alkyl acrylates such as 2-cyanoethyl acrylate (Tg 4° C.); (3) methacrylic monomers including (a) alkyl methacrylates such as butyl methacrylate (Tg 20° C.), hexyl methacrylate (Tg −5° C.), 2-ethylhexyl methacrylate (Tg −10° C.), octyl methacrylate (Tg −20° C.), dodecyl methacrylate (Tg −65° C.), hexadecyl methacrylate (Tg 15° C.) and octadecyl methacrylate (Tg −100° C.) and (b) aminoalkyl methacrylates such as diethylaminoethyl methacrylate (Tg 20° C.) and 2-tert-butyl-aminoethyl methacrylate (Tg 33° C.); (4) vinyl ether monomers including (a) alkyl vinyl ethers such as methyl vinyl ether (Tg −31° C.), ethyl vinyl ether (Tg −43° C.), propyl vinyl ether (Tg −49° C.), butyl vinyl ether (Tg −55° C.), isobutyl vinyl ether (Tg −19° C.), 2-ethylhexyl vinyl ether (Tg −66° C.) and dodecyl vinyl ether (Tg −62° C.); (5) cyclic ether monomers include tetrahydrofuran (Tg −84° C.), trimethylene oxide (Tg −78° C.), ethylene oxide (Tg −66° C.), propylene oxide (Tg −75° C.), methyl glycidyl ether (Tg −62° C.), butyl glycidyl ether (Tg −79° C.), allyl glycidyl ether (Tg −78° C.), epibromohydrin (Tg −14° C.), epichlorohydrin (Tg −22° C.), 1,2-epoxybutane (Tg −70° C.), 1,2-epoxyoctane (Tg −67° C.) and 1,2-epoxydecane (Tg −70° C.); (6) ester monomers (other than the above acrylates and methacrylates) including ethylene malonate (Tg −29° C.), vinyl acetate (Tg 30° C.), and vinyl propionate (Tg 10° C.); (7) halogenated alkene monomers including vinylidene chloride (Tg −18° C.), vinylidene fluoride (Tg −40° C.), hexafluoropropylene, tetrafluoroethylene, cis-chlorobutadiene (Tg −20° C.), and trans-chlorobutadiene (Tg −40° C.); and (8) siloxane monomers including dimethylsiloxane (Tg −127° C.), diethylsiloxane, methylethylsiloxane, methylphenylsiloxane (Tg −86° C.), and diphenylsiloxane.

Specific examples of high Tg polymer blocks include homopolymer and copolymer blocks containing one or more of the following: (1) vinyl aromatic monomers including (a) unsubstituted vinyl aromatics, such as styrene (Tg 100° C.) and 2-vinyl naphthalene (Tg 151° C.), (b) vinyl substituted aromatics such as alpha-methyl styrene, and (c) ring-substituted vinyl aromatics including ring-hydroxylated vinyl aromatics such as 4-hydroxystyrene (Tg 174° C.), ring-alkylated vinyl aromatics such as 3-methylstyrene (Tg 97° C.), 4-methylstyrene (Tg 97° C.), 2,4-dimethylstyrene (Tg 112° C.), 2,5-dimethylstyrene (Tg 143° C.), 3,5-dimethylstyrene (Tg 104° C.), 2,4,6-trimethylstyrene (Tg 162° C.), and 4-tert-butylstyrene (Tg 127° C.), ring-alkoxylated vinyl aromatics, such as 4-methoxystyrene (Tg 113° C.) and 4-ethoxystyrene (Tg 86° C.), ring-halogenated vinyl aromatics such as 2-chlorostyrene (Tg 119° C.), 3-chlorostyrene (Tg 90° C.), 4-chlorostyrene (Tg 110° C.), 2,6-dichlorostyrene (Tg 167° C.), 4-bromostyrene (Tg 118° C.) and 4-fluorostyrene (Tg 95° C.), ring-ester-substituted vinyl aromatics such as 4-acetoxystyrene (Tg 116° C.), ring-amino-substituted vinyl aromatics including 4-amino styrene, ring-silyl-substituted styrenes such as p-dimethylethoxy siloxy styrene, unsubstituted and substituted vinyl pyridines such as 2-vinyl pyridine (Tg 104° C.) and 4-vinyl pyridine (Tg 142° C.), and other vinyl aromatic monomers such as vinyl carbazole (Tg 227° C.) and vinyl ferrocene (Tg 189° C.); (2) other vinyl monomers including (a) vinyl esters such as vinyl benzoate (Tg 71° C.), vinyl 4-tert-butyl benzoate (Tg 101° C.), vinyl cyclohexanoate (Tg 76° C.), vinyl pivalate (Tg 86° C.), vinyl trifluoroacetate (Tg 46° C.), vinyl butyral (Tg 49° C.), (b) vinyl amines, (c) vinyl halides such as vinyl chloride (Tg 81° C.) and vinyl fluoride (Tg 40° C.), and (d) alkyl vinyl ethers such as tert-butyl vinyl ether (Tg 88° C.) and cyclohexyl vinyl ether (Tg 81° C.); (3) other aromatic monomers including acenaphthalene (Tg 214° C.) and indene (Tg 85° C.); (4) methacrylic monomers including (a) methacrylic acid anhydride (Tg 159° C.), (b) methacrylic acid esters (methacrylates) including (i) alkyl methacrylates such as methyl methacrylate (Tg 105-120° C.), ethyl methacrylate (Tg 65° C.), isopropyl methacrylate (Tg 81° C.), isobutyl methacrylate (Tg 53° C.), t-butyl methacrylate (Tg 118° C.) and cyclohexyl methacrylate (Tg 92° C.), (ii) aromatic methacrylates such as phenyl methacrylate (Tg 110° C.) and including aromatic alkyl methacrylates such as benzyl methacrylate (Tg 54° C.), (iii) hydroxyalkyl methacrylates such as 2-hydroxyethyl methacrylate (Tg 57° C.) and 2-hydroxypropyl methacrylate (Tg 76° C.), (iv) additional methacrylates including isobornyl methacrylate (Tg 110° C.) and trimethylsilyl methacrylate (Tg 68° C.), and (c) other methacrylic-acid derivatives including methacrylonitrile (Tg 120° C.); (5) acrylic monomers including (a) certain acrylic acid esters such as tert-butyl acrylate (Tg 43-107° C.), hexyl acrylate (Tg 57° C.) and isobornyl acrylate (Tg 94° C.); and (b) other acrylic-acid derivatives including acrylonitrile (Tg 125° C.).

In certain embodiments, the hydrophobic/hydrophilic balance of a given polymer block is altered by including a hydrophilic co-monomer within the block.

As used herein, a poly(vinyl aromatic) block is a block that contains multiple copies of one or more types of vinyl aromatic monomers, a polyalkene block is a block that contains multiple copies of one or more types of alkene monomers, and so forth.

As noted above, the medical devices of the present invention contain at least one covalently crosslinked polymeric region, which contains at least one block copolymer. The at least one block copolymer further contains (a) at least one low Tg block and (b) at least one high Tg block. For example, two or more high Tg blocks may be interconnected through one or more low Tg blocks, among many other possibilities.

Covalent crosslinking has been shown to increase the strength and elongation of triblock copolymers. See, e.g., S. Sakurai et al., "Mechanical properties of polystyrene-block-polybutadiene-block-polystyrene triblock copolymers crosslinked in the disordered state," *Polymer* 40 (1999) 2071-2076. Crosslinking is also expected to improve further mechanical properties including, for example, one or more of creep resistance, abrasion resistance and tear resistance, among others. Improvement in mechanical properties will improve the performance of various medical devices.

In some embodiments, one or more blocks within the block copolymer itself are sufficiently reactive to undergo crosslinking. In other embodiments, the block copolymer is modified to render it sufficiently reactive. In still other embodiments, reactive species are introduced during the polymerization process to render the block copolymer sufficiently reactive. In yet other embodiments, the block copolymer is blended with a supplemental reactive polymer, which is then crosslinked, thereby forming an interpenetrating network.

Polymers may be crosslinked in a variety of ways. For instance, crosslinking may be initiated by exposure to energy (e.g., the application of heat or ionizing or non-ionizing radiation such as e-beam radiation, gamma radiation, UV light, visible light, etc.) or a chemical agent (e.g., moisture), or both. Crosslinking may progress with the aid of suitable chemical species, for example, catalysts (e.g., species that aid in completion of a chemical reaction without becoming part of the reaction product) and/or crosslinking agents (e.g., species which form bonds with other molecules and which become part of the crosslinked polymer network), among others. Polymers may be crosslinked after their formation or at the time of their formation.

As a first example, various polyalkenes, including polymers formed from ethylene and/or propylene, among others, can undergo crosslinking as a result of the formation of radical species along their backbones. Radicals may form, for example, upon exposure to ionizing radiation (e.g., from high energy electrons, x-rays, gamma radiation, and so forth). Radicals may also form upon exposure to free-radical generating species such as peroxides, peresters, and azo compounds, among others, with peroxides such as the following being commonly used: 2,5-dimethyl-2,5-bis(t-butylperoxy)-3-hexyne (Lupersol 130, Atochem Inc., Philadelphia, Pa.); 2,5-dimethyl-2,5-di-(t-butylperoxy)-hexane (Varox 130); t-butyl alpha-cumyl peroxide; di-butyl peroxide; t-butyl hydroperoxide; benzoyl peroxide; dichlorobenzoyl peroxide; dicumyl peroxide (Lupersol 101, Atochem Inc.); di-t-butyl peroxide; 2,5 dimethyl-2,5-di(peroxy benzoate)-3-hexyne; 1,3-bis(t-butyl peroxy isopropyl)benzene; lauroyl peroxide; di-t-amyl peroxide; 1,1-di-(t-butylperoxy)cyclohexane; 2,2-di-(t-butylperoxy) butane; and 2,2-di-(t-amylperoxy) propane.

Once formed, radicals on two different chains may combine to form a bond between the chains. This reaction is may be enhanced when the polymer is in a mobile state, for example, in a melt state, which state may be established concurrently with radical formation, or subsequent to radical formation.

Based on these principles, polyalkene block copolymers (e.g., triblock copolymers having high Tg endblocks and having low Tg centerblocks that contain ethylene, propylene or both, etc.) may be crosslinked by exposure to radiation or free-radical-forming compounds, for instance, while in the melt stage. Commercially available examples of block copolymers of this type include, for instance, KRATON G series polymers from Kraton Polymers, Houston Tex., USA, specifically SEBS, a poly(styrene-b-ethylene/butylene-b-styrene) triblock copolymer (e.g., KRATON G 1650, 1651, 1652, 1654, 1657, etc.). As one specific example, such a copolymer may be heated in a mold (e.g., corresponding in shape to the desired medical device or device component) to the melt stage and then crosslinked, for example, by applying ionizing radiation or by including a free-radical generating species that is activated upon heating to the melt stage.

In addition to being reactive with one another, radicals created on polymer chains are also reactive with various additional species, including multifunctional crosslinking species, such as those having one or more sites of unsaturation (e.g., —HC=CH— or —C≡C—).

For example, in some embodiments of the invention, vinyl crosslinking agents may be added to enhance crosslinking between the radicalized block copolymers. For instance, alkenes such as HC=CH—(CH$_2$)$_n$—HC=CH, where n is an integer, for example, ranging from 0 to 20, may be used for this purpose. In this regard, see, e.g., P. Bracco et al., infra, in which ultra high molecular weight polyethylene soaked in 1,7-octadiene, among other species, is crosslinked upon exposure to electron beam radiation. Such radicals may also be generated by the introduction of free radical generating compounds such as peroxides as noted above.

Other examples of multifunctional crosslinking agents include terminally unsaturated, linear or branched, polymers, for example, polyalkenes (e.g., polyethylene, polybutylene, poly(ethylene-co-polybutylene), polyisobutylene, etc.), polyvinyl aromatics, polysiloxanes, polyacrylates, polymethacrylates, and so forth, which polymers may contain, for example, from 2 to 5 to 10 to 25 to 50 to 100 or more monomer units. Certain of these polymers (e.g., polyisobutylene and polymethacrylates) are susceptible to chain scission upon exposure to radiation.

In this regard, compatibility between the crosslinking agents and the block copolymers may be enhanced by using multifunctional crosslinking agents that contain polymer blocks which have the same or similar monomer composition as is found in the block copolymer to be crosslinked. For instance, SEBS may be crosslinked using terminally unsaturated polyethylene, polybutylene, poly(ethylene-co-butylene) or polystyrene.

Polymer blocks that contain one or more types of diene monomer are particularly amenable to crosslinking, including chemical based crosslinking (e.g., using free-radical generating species), energy based crosslinking (e.g., using ionizing or non-ionizing radiation) or both. Dienes for forming polymer blocks may be selected, for example, from suitable members of those described above, among others. Specific examples of block copolymers include poly(styrene-b-isoprene-b-styrene) (SIS) and poly(styrene-b-butadiene-b-polystyrene) (SBS) triblock copolymers, among others.

As a specific example, R. Basheer et al., "The radiation crosslinking of block copolymers of butadiene and styrene," *Die Makromolekulare Chemie*, 2003, Volume 183, Issue 9, 2141-2151 describe a process whereby block copolymers of butadiene and styrene are crosslinked by exposure to gamma radiation. Crosslinking of SBS and SIS by electron beam radiation is described in H. Kanbara et al., "Measurement of crosslinking degree for electron beam irradiated block copolymers," *Polymer Engineering and Science*, 2004, Volume 34, Issue 8, pp. 691-694. As another specific example, S. Sakurai et al., "Mechanical properties of polystyrene-block-polybutadiene-block-polystyrene triblock copolymers crosslinked in the disordered state," *Polymer* 40 (1999) 2071-2076 demonstrated that SBS may be crosslinked using a peroxide agent, specifically 1,1-bis(tert-butylperoxy)-3,3,5-trimethylcyclohexane. As a further specific example, C. Decker, et al., "High-speed photocrosslinking of thermoplastic styrene-butadiene elastomers," *Journal of Applied Polymer Science*, 2000, Volume 77, Issue 9, 1902-1912, report the crosslinking of SBS and SIS copolymers using an acylphosphine oxide photoinitiator and a trifunctional thiol crosslinking agent. Decker et al. also report the photocrosslinking of SBS upon UV exposure in the presence of an acylphosphine oxide photoinitiator and, optionally, a telechelic acrylate oligomer in *Macromolecular Chemistry and Physics*, "Photocrosslinking of functionalized rubbers, 7. Styrene-butadiene block copolymers," 1999, Volume 200, Issue 2, Pages 358-367.

In other embodiments, polymers are rendered crosslinkable by providing them with readily crosslinkable groups, either during or subsequent to polymerization of the same. Crosslinkable groups may be provided at one or more chain ends of the polymer, along the polymer backbone(s) of the polymer, or a combination of both.

For example, silane compounds that have a combination of unsaturated and hydrolyzable groups may be grafted, for example, onto polyalkenes (e.g., polymers containing ethylene and/or butylene) under free radical generating conditions (e.g., in the presence of a suitable peroxide or in the presence of ionizing radiation). As a specific example, vinyl trimethoxysilane has been grafted to polyethylene using dicumyl peroxide as the grafting agent. Such polymers are moisture curable (crosslinkable). In particular, crosslinking may proceed upon exposure to water, which causes the alkoxy groups in the polymer to be hydrolyzed, followed by condensation of neighboring hydroxyl groups to form the crosslinks containing —Si—O—Si— linkages. This process may be promoted, for example, by steam autoclaving or through the use of a suitable catalyst, for example an organo-tin catalyst.

Using analogous processes, in accordance with the invention, block copolymers with polymer blocks containing, for example, ethylene, propylene or both, may be crosslinked with species having one or more sites of unsaturation and one or more hydrolysable silane groups. Specific examples of such silanes, among others, include species of the formula HC=CH—(CH$_2$)$_n$—Si—(OR)$_3$, where n is an integer, for example, ranging from 0 to 20, and R is selected from alkyl groups having 1 to 10 carbon atoms and aryl groups having 6 to 10 carbon atoms.

As another example, crosslinking may be achieved by first hydrosilylating an ethylene propylene diene monomer (EPDM) rubber with a silane compound, whereupon the silicon hydride bond (Si—H) reacts with the pendant olefinic unsaturation found in the EPDM rubber. The silane also preferably contains multiple alkylsiloxy groups for subsequent crosslinking reactions. An example of such a compound is tris(trimethylsiloxy)silane available from Sigma-Aldrich and Gelest, Inc. Morrisville, Pa., USA (product # SIT8721.0).

It is also known to graft unsaturated acid anhydrides onto polymer chains, including those containing ethylene or propylene. For instance, it is known to graft of maleic anhydride onto polyalkene chains in the presence of organic peroxides. Examples of peroxides are listed above. Maleation of polyalkene chains may be performed, for example, in solution or in the melt phase (e.g., by reactive extrusion, etc.), among other processes.

Using analogous processes, block copolymers containing ethylene, propylene or both, may be maleated. Block copolymers of this type are commercially available. For example, maleated SEBS is available from Kraton Polymers as Kraton FG series polymers (e.g., FG1901 or FG1924X). Such maleated polymers may then be crosslinked via multifunctional crosslinking species, each containing two or more groups that are reactive with the grafted anhydride groups, for example, amine groups and/or hydroxyl groups, among others. Examples of such species include multifunctional alcohols, multifunctional amines, linear or branched polyalkenes with terminal hydroxyl and/or amine groups, linear or branched poly(vinyl aromatics) with terminal hydroxyl and/or amine groups, and so forth.

After crosslinking, any residual maleic anhydride units can be hydrolyzed to form carboxylates (carboxylic acid groups). These groups can form hydrogen bonds which can also act as physical crosslinks.

Further information concerning crosslinking of polyalkenes may be found, for example, in P. Bracco et al., "Radiation-induced crosslinking of UHMWPE in the presence of co-agents: chemical and mechanical characterization," *Polymer* 46 (2005) 10648-10657, G. Lewis, "Properties of crosslinked ultra-high-molecular-weight polyethylene," *Biomaterials* 22 (2001) 371-401, S. M. Kurtz et al., "Advances in the processing, sterilization, and crosslinking of ultra-high molecular weight polyethylene for total joint arthroplasty," Biomaterials 20 (1999) 1659-1688, U.S. Pat. No. 4,036,719 to Lyons, U.S. Patent App. No. 2005/0031813 to Cornette et al., U.S. Patent App. No. 2005/0218551 to Halahmi et al., and U.S. Pat. App. No. 2004/0208841 to Salovey et al., the disclosures of which are hereby incorporated by reference.

As another example, dienes can also be reacted with peroxy acids to form epoxy groups, which can be crosslinked by treatment with radiation. One study, in which epoxidized natural rubber was crosslinked via irradiation, found that most of the crosslinking was due to epoxy group ring opening, and very little or no C—C crosslinking was observed. M C Senake Perera, "Radiation degradation of epoxidized natural rubber studied by solid-state nuclear magnetic resonance and infrared spectroscopy," *Polymer International* Volume 49, Issue 7, 2000, Pages 691-698. If desired, the dienes may be partially hydrogenation prior to formation of epoxy groups, as described in U.S. Pat. No. 5,491,193 to Erickson. For example, in Erickson, polymers are hydrogenated to produce a partially hydrogenated polymer which has remaining about 0.1 to about 5 milliequivalents per gram of polymer of residual aliphatic double bonds. The partially hydrogenated polymer is contacted with a peroxy acid to form an epoxidized polymer, which has between 0.1 and about 5 milliequivalents of epoxide per gram of polymer. The epoxidized polymer is then exposed to an amount of radiation (either ionizing or non-ionizing) sufficient to crosslink the polymer.

In other embodiments, polydienes may be epoxidized to the desired degree, followed by crosslinking and then hydrogenation to reduce/remove residual unsaturation.

In other embodiments, poly(vinyl aromatic) blocks, including polystyrene blocks associated with block copolymers having low Tg midblocks and polystyrene end blocks (e.g., SIBS, SEBS, poly[styrene-b-n-butyl-acrylate-b-styrene], poly[styrene-b-dimethylsiloxane-b-styrene], poly[styrene-b-fluorinated olefin-b-styrene], etc.), may be crosslinked using various techniques, including, for example, the inclusion of crosslinkable groups at the ends of the polystyrene blocks or inclusion of one or more crosslinkable groups along the length of the polystyrene blocks.

For example, a SIBS triblock copolymer containing chloromethyl groups in the styrene end-blocks may be prepared, for instance, as described in S. Itsuno et al., *J. Am. Chem. Soc.* 1990, 112, 8187-88, who report the formation of poly(styrene-co-chloromethyl styrene) via the chloromethylation of a portion of the styrene monomers within liner polystyrene using trioxane and chloromethylsilane in the presence of stannic chloride.

The chloromethyl styrene groups in the end-blocks can then be crosslinked, for instance, in the presence of a diamine. For example, Y. Sakai et al., "Humidity sensor durable at high humidity using simultaneously crosslinked and quaternized poly(chloromethyl styrene)," *Sensors and Actuators B: Chemical*, 25(1-3), 1995, pp. 689-691, report the simultaneous crosslinking and quaternization of poly(chloromethyl styrene) by reaction with N,N,N',N'-tetramethyl-1,6-hexanediamine. Various N,N,N',N'-tetraalkyl-α,ω-alkanediamines in addition to N,N,N',N'-tetramethyl-1,6-hexanediamine may also be used, such as N,N,N',N'-tetramethyl-1,2-ethylenediamine, N,N,N',N'-tetraethyl-1,2-ethylenediamine, N,N,N',N'-tetramethyl-1,3-propanediamine, N,N,N',N'-tetraethyl-1,3-propanediamine, N,N,N',N'-tetramethyl-1,4-butanediamine, N,N,N',N'-tetraethyl-1,4-butanediamine, N,N,N',N'-tetramethyl-1,5-pentanediamine, N,N,N',N'-tetraethyl-1,5-pentanediamine, N,N,N',N'-tetraethyl-1,6-hexanediamine, N,N,N',N'-tetramethyl-1,8-octanediamine, N,N,N',N'-tetraethyl-1,8-octanediamine, N,N,N',N'-tetramethyl-1,10-decanediamine, N,N,N',N'-tetraethyl-1,10-decanediamine, to name a few.

Other methods for crosslinking polystyrene blocks are based on the formation and crosslinking of alkoxysilane-derived polystyrene blocks.

T. Higashihara et al., *Polymer Preprints*, 2007, 48(2), 1037, describe the formation of chloromethylated SIBS (using the method of S. Itsuno et al., supra), followed allylation of the chloromethylated SIBS, and hydrosilation of the allyl-functionalized SIBS with silyl hydride functionalized poly(dimethyl siloxane).

In an embodiment of the present invention, on the other hand, allyl functional groups of an allyl-functionalized SIBS copolymer may be hydrosilylated with a suitable silane, for example, a silane containing multiple alkyloxy or aryloxy groups for subsequent crosslinking reactions. Specific examples of such silanes, among others, include species of the formula H$_{4-n}$—Si—(OR)$_n$, where n is 2 or 3 and R is selected from alkyl groups having 1 to 10 carbon atoms and aryl groups having 6 to 10 carbon atoms (i.e., a dialkoxysilane, diaryloxysilane, a trialkoxysilane or a triaryloxysilane), for instance, trimethoxysilane, to name a specific example. The resulting hydrosilylated SIBS may then be crosslinked in the presence of moisture, optionally in the presences of additional agents such as, for instance, catalysts (e.g., organo-tin catalysts such as tin(II)-2-ethylhexanoate, among others) and/or crosslinking agents.

Silanes with functional groups other than alkoxy or aryloxy groups, such as, for instance, anhydride, epoxy, amine, carboxylate, phosphonate, sulfonate, hydroxyl, isocyanate, halogen or azide groups, among others, are also available and are capable of being used in crosslinking reactions Other embodiments of the invention involve the incorporation of reactive species in conjunction with the polymerization process.

In this regard, cationic polymerization of unsaturated monomers, including alkenes such as isobutylene, butadiene, isoprene, methylbutene, and 2-methylpentene, among others, or vinyl aromatic monomers, such as styrene, p-methylstyrene, alpha-methylstyrene and indene, among others, is well known. In a typical cationic polymerization process a suitable unsaturated monomer is polymerized in the presence of a cationic polymerization catalyst, an initiator, and an optional Lewis base (in order to prevent initiation by protic impurities), typically in an aprotic solvent under dry conditions at low temperature. The polymers formed in this method are living cationic polymers (e.g., polymers in which the polymer chains typically continue to grow from the site of initiation until the monomer supply is exhausted, rather than terminating when the chain reaches a certain length or when the catalyst is exhausted). The cationic polymerization catalyst may be, for example, a Lewis acid (e.g., $BCl_3$ or $TiCl_4$, among others). The initiator may be, for example, an alkyl halide or (haloalkyl)-aryl compound, for example, a monofunctional initiator such as 2-chloro-2,4,4-trimethylpentane, a bifunctional initiator such as 1,3-di(1-chloro-1-methylethyl)-5-(t-butyl)benzene, or a trifunctional initiator such as 1,3,5-tri(1-chloro-1-methylethyl)benzene, among others. Lewis bases include pyridine and its derivatives, such as 2,6-ditert-butyl-pyridine (DTBP) or lutidine, among others.

As a specific example, a cationically polymerizable alkene such as isobutylene may be polymerized in the presence of a bifunctional initiator (e.g., 1,3-di(1-chloro-1-methylethyl)-5-(t-butyl)benzene, among others) followed by continued polymerization of a cationically polymerizable vinyl aromatic monomer such as styrene from the two polyalkene chain ends, thereby forming a poly(vinyl aromatic-b-alkene-b-vinyl aromatic) triblock copolymer (the presence of the initiator residue is typically ignored in block copolymer terminology as it is a minor component of the copolymer).

To render a poly(vinyl aromatic-b-alkene-b-vinyl aromatic) copolymer such as SIBS more reactive, and thus better able to participate in crosslinking reactions, a small amount of a diene, for instance, isoprene or butadiene, may be added (e.g., admixed with the isobutylene or added subsequent to the isobutylene) during the cationic polymerization process, thereby yielding SIBS having unsaturation within the polyisobutylene blocks or at the ends thereof. Such a polymer can then be crosslinked, for example, using techniques such as those described above for use in conjunction with EPDM rubber, among others.

In some embodiments, polymer blocks are crosslinked simultaneously with their formation (or with their chain extension) using multifunctional monomers. For instance, polystyrene blocks (e.g., polystyrene endblocks for a low Tg midblock) may be crosslinked simultaneously with their formation or with their extension by polymerization or chain extension of the polystyrene blocks using a mixture of styrene and a difunctional vinyl monomer such as divinyl benzene. See U.S. Pat. No. 6,471,955.

As another example, multifunctional macromonomers having two or more unsaturated functional groups (e.g., allyl, acrylate, etc.) may be employed in polymerization reactions to yield crosslinked products. For example, allyl-functionalized SIBS such as that described above in T. Higashihara et al. or linear polyisobutylene or SIBS end-capped with allyl terminal groups, may be employed as macromonomers in a polymerization step (e.g., with a suitable comonomer such as styrene, among others). Alternatively, a block copolymer may be crosslinked by copolymerization of a macromonomer having a single unsaturated group and a comonomer having multiple unsaturated groups.

As another example in which block copolymers are rendered more reactive by end-capping them with reactive compounds, block copolymers may be end-capped with heterocyclic compounds, which may then be crosslinked by UV in the presence of a photoinitiator. In this regard, U.S. Pat. No. 6,750,267 to Faust et al, which is hereby incorporated by reference, describes isobutylene polymers, end-capped with heterocyclic compounds, which may be combined with a cationic photoinitiator (e.g., an onium salt selected from diaryliodonium salts of sulfonic acids, triarylsulfonium salts of sulfonic acids, diaryliodonium salts of boronic acids, and triarylsulfonium salts of boronic acids, among others) and exposed to an energy source such as ultraviolet light or visible light in an amount sufficient to cure (i.e., crosslink) the composition.

Triblock copolymers for use in the present invention may be formed, for example, by cationically polymerizing a first monomer (e.g., isobutylene) from a bifunctional initiator (e.g., 1,3-di(1-chloro-1-methylethyl)-5-(t-butyl)benzene), followed by cationic polymerization of a second monomer (e.g., styrene). The polymerization is terminated prior to complete conversion of the styrene monomer. The triblock copolymer thus formed, for example, poly(styrene-b-isobutylene-b-styrene), may then be isolated/purified, followed by end-capping with a heterocyclic compound (e.g., 2,2-difurylpropane or thiophene, among others) via a process like than described in Faust et al. The end-capped polymers may then be combined with cationic photoinitiator and crosslinked by exposure to energy source (e.g., ultraviolet light).

As another example, block polymers may be prepared, which have reactive groups at one or more chain ends, along one or more chains, or a combination thereof.

As a specific example, U.S. Pat. No. 5,981,895, U.S. Pat. No. 6,051,657 and U.S. Pat. No. 6,194,597, each to Faust et al. and hereby incorporated by reference, describe methods for preparing silyl-functional living cationic polymers which can be coupled to one another to form a moisture-curable telechelic system. The methods utilize a functional initiator for the polymerization process, followed by a coupling the chain ends together using a di-functional linking agent to form a moisture curable polymer. More particularly, the methods described comprise reacting, in the presence of a Lewis acid, at least one cationically polymerizable monomer with a functional initiator which comprises a typical cationic polymerization initiation group (e.g., a halogen, alkoxy, acyloxy or hydroxyl group) and a silane group (e.g., $-SiX_nR_{3-n}$, wherein R is selected from alkyl groups having 1 to 10 carbon atoms or aryl groups having 6 to 10 carbon atoms, X is halogen, and n is 1, 2 or 3), for instance,

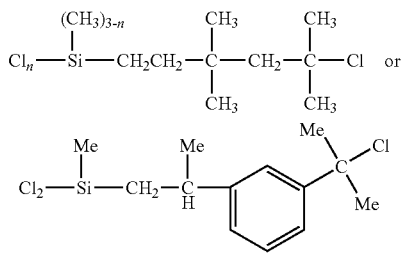

among others. The resulting living polymer is then coupled using a suitable coupling agent, for example, a molecule having at least two furan rings, for instance,

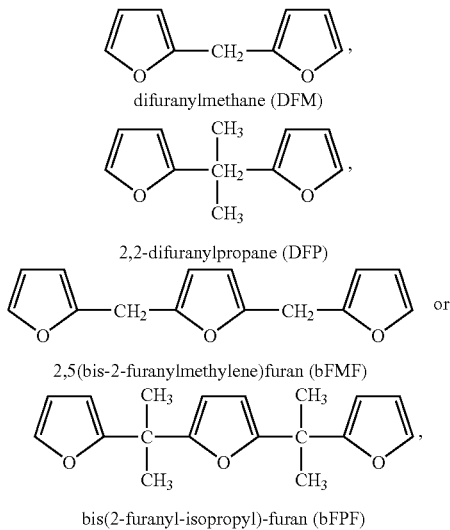

among others.

According to one embodiment, copolymers for use in the present invention may be prepared, for example, by polymerization of a first cationically polymerizable high Tg monomer (e.g., a vinyl aromatic monomers such as styrene) from a silyl functional initiator, followed by polymerization of a second low Tg monomer (e.g., an alkene such as isobutylene). The resulting silyl functionalized diblock copolymer may then be coupled to itself with a suitable coupling agent, for example, a molecule having at least two furan rings such as those described above, among others. The resulting HLH triblock copolymer (this terminology ignores the presence of the initiator and coupling group residues, as noted above) is then reacted with an alcohol (e.g., methanol, ethanol, propanol, butanol, etc.), whereby the halogen groups on silicon atoms are replaced by an alkoxy functionality that corresponds to the alcohol. The resulting alkoxysilyl-functional polymer may then be isolated from the reaction solution by conventional means, such as precipitation with a non-solvent. Such polymers may be cured by exposure to moisture, and they may optionally contain additional agents such as, for instance, catalysts (e.g., organo-tin catalysts such as tin(II)-2-ethylhexanoate, among others) and/or crosslinking agents.

Moisture curable polymers are also described in U.S. Pat. No. 6,469,115 to Faust et al., which is hereby incorporated by reference, in which cationic polymerization of an alkene, such as isobutylene, is conducted in the presence of a silyl functional initiator, for example, one of those described above. Moreover, a silyl-functional vinyl aromatic monomer is also employed in the polymerization process such as,

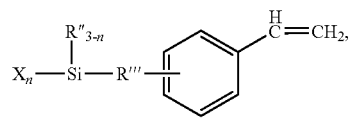

where R″ is independently selected from alkyl groups having 1 to 10 carbon atoms or aryl groups having 6 to 10 carbon atoms, R′″ is a divalent non-aromatic hydrocarbon group having 2 to 6 carbon atoms, X is a halogen group, and n is independently 1, 2 or 3, for example, 2-dichlorolmethylsilyl-ethyl-styrene (DSiSt). In some embodiments, the alkene monomer is polymerized first, followed by polymerization of the silyl-functional monomer after the alkene polymerization is essentially complete. In other embodiments, the alkene monomer and silyl-functional monomer are polymerized simultaneously. In either case, as discussed above, the resulting polymers is then reacted with an alcohol, and the resulting alkoxysilyl-functional polymer is isolated. Such polymers may be crosslinked by exposure to moisture, optionally in the presence of additional agents such as, for instance, catalysts and/or crosslinking agents.

Polymers for use in the present invention may be made using analogous procedures. For instance, a silyl-functional initiator, for example, one of those described above (which are mono-functional for purposes of cationic polymerization) may be employed, with high Tg monomer polymerization proceeding before low Tg monomer polymerization. A silyl-functional vinyl monomer, for example, one of those described above may be introduced at one or more points in the process, for example, introduced before the high Tg monomer, introduced admixed with the high Tg monomer, introduced after the high Tg monomer and before the low Tg monomer, introduced admixed with the low Tg monomer, introduced after the low Tg monomer, as well as any combination of the foregoing. For example, styrene polymerization may proceed from the silyl-functional initiator, followed by isobutylene polymerization, followed by polymerization of a silyl-functional vinyl aromatic monomer. As another example, styrene polymerization may proceed from a silyl-functional initiator, followed by polymerization of a silyl-functional vinyl aromatic monomer, followed by isobutylene polymerization. Regardless of the embodiment, the resulting polymers may be coupled to one another, for example, using a molecule having at least two furan rings, for instance, bFPF, as described above. The resulting coupled polymer may then be reacted with an alcohol, and the resulting alkoxysilyl-functional polymer isolated. Such polymers may be crosslinked by exposure to moisture, optionally in the presence of additional agents such as, for instance, catalysts and/or crosslinking agents.

As another example, a difunctional initiator may be employed, with low Tg monomer polymerization proceeding before high Tg monomer polymerization. A silyl-functional vinyl aromatic monomer like those described above may be introduced at one or more points in the process, for example, introduced before the low Tg monomer, introduced admixed with the low Tg monomer, introduced after the low Tg monomer and before the high Tg monomer, introduced admixed with the high Tg monomer, introduced after the high Tg monomer, as well as any combination of the foregoing. As a first example, isobutylene polymerization may proceed from a difunctional initiator, followed by styrene polymerization, followed by polymerization of a silyl-functional vinyl aromatic monomer. As a second example, isobutylene polymerization may proceed from a difunctional initiator, followed by polymerization of a silyl-functional vinyl aromatic monomer, followed by styrene polymerization. As a third example, polymerization or a mixture of isobutylene and silyl-functional vinyl aromatic monomer may proceed from a difunctional initiator, followed by polymerization styrene. Regardless of the embodiment, the resulting polymers may be reacted with an alcohol, isolated, and crosslinked by exposure to moisture, optionally in the presence of additional agents such as, for instance, catalysts and/or crosslinking agents, as described above.

Further moisture curable polymers are described in U.S. Pat. No. 6,268,451 to Faust et al., which is hereby incorporated by reference, in which the following three monomers are simultaneously polymerized in the presence of a Lewis acid and a solvent: (a) an alkene monomer, for example, isobutylene, (b) a first silyl-functional vinyl aromatic that is much more reactive than the alkene monomer, for example, a vinylphenyl monomer such as

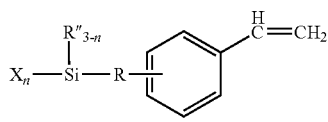

and (c) a second silyl-functional vinyl aromatic that is much less reactive than the alkene monomer, for example, an alpha-alkyl-substituted vinylphenyl monomer such as

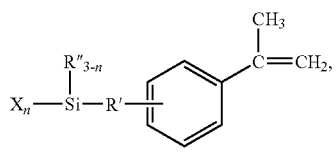

where R and R' are divalent non-aromatic hydrocarbon groups having 2 to 6 carbon atoms, R" is selected from alkyl groups having 1 to 10 carbon atoms or aryl groups having 6 to 10 carbon atoms, X is independently a hydrolyzable group such as a halogen group, and n is independently 1, 2 or 3. The resulting polymer is said to be a "pseudo-telechelic" terpolymer, which denotes a copolymer having one type of reactive silyl-functional unit statistically concentrated near the head of the terpolymer chain and a slightly different type of reactive silyl-functional unit statistically concentrated at the tail of the terpolymer. Such polymers may be reacted with an alcohol, isolated, and crosslinked by exposure to moisture as described above.

In certain embodiments of the invention, an interpenetrating polymer network (IPN) or a semi-IPN is created in which where a supplemental polymer is crosslinked in the presence of a block copolymer that contains (a) at least one low Tg block and (b) at least one high Tg block. Without wishing to be bound by theory, it is believed that by crosslinking the supplemental polymer, the block copolymer is anchored into the crosslinked polymeric region through covalent crosslinks (if the block copolymer is reactive), chain entanglement, or both.

Examples of supplemental polymers may be selected from polymers that crosslink upon exposure to radiation, heat and/ or a chemical agent such as moisture or polymers that are crosslinked at the time of formation due the presence of a multifunctional comonomer. Specific examples of such polymers include homopolymer and copolymers that contain alkene units, for example, olefin units such as ethylene and/and propylene units, or diene units such as isoprene and/or butadiene units, among others. As noted above, such polymers may be crosslinked, for example, upon exposure to energy or a chemical curing agent, optionally after having undergone chemical reaction to create reactive groups along the polymer backbone (e.g., alkoxysilane groups, anhydride groups, epoxy groups, etc.), optionally in the presence of catalysts (e.g., peroxides, photoinitiators, etc.) and/or optionally in the presence of crosslinking agents (e.g., multifunctional species such as those with vinyl, thiol, hydroxyl and/or amine groups, among others). Further specific examples include crosslinkable polymers which are formed using functional initiators (e.g., silyl functional initiators, among many others), which contain functional monomers (e.g., silyl-functional monomers, chloromethyl monomers, maleic anhydride monomers, among many others), and/or which contain functional endcaps (e.g., heterocyclic compounds, silyl-functional endcaps, among many others). Examples of supplemental polymers may also be selected from polymers that are crosslinked at the time of formation due the presence of a multifunctional comonomer (e.g., a supplemental polymer formed from co-polymerization of styrene and divinylbenzene in the presence of a block copolymer, among many others). Further information regarding these specific examples is discussed above, and is applicable to homopolymers and copolymers other than the block copolymers exemplified.

As a specific example, a crosslinkable supplemental polymer, for instance, a homopolymer such as poly(chloromethyl styrene), poly(maleic anhydride), polyethylene or polybutylene, or a copolymer such as poly(chloromethyl styrene-co-styrene), poly(styrene-co-maleic anhydride), polyethylene-co-polybutylene or polyethylene-co-butylacrylate, may be crosslinked in the presence of (a) a triblock copolymer having a reactive low Tg midblock and high Tg endblocks, for example, the SEBS copolymer, or (b) a triblock copolymer having a nonreactive low Tg midblock and high Tg endblocks, for example, the SIBS copolymer. Optionally, crosslinking may proceed after generating reactive groups along the polymer backbone (e.g., alkoxysilane groups and anhydride groups as discussed above, among others), in the presence of catalysts (e.g., peroxides and photoinitiators as discussed above, among others), and/or in the presence of crosslinking agents (e.g., multifunctional species such as those with vinyl, hydroxyl or amine groups as discussed above, among others). Without wishing to be bound by theory, it is believed that the SEBS may become anchored into the crosslinked polymeric region through a combination of covalent crosslinks and chain entanglement, whereas the SIBS may become anchored into the crosslinked polymeric region through chain entanglement.

In certain embodiments, one or more therapeutic agents are provided on, within or beneath the crosslinked polymeric regions in accordance with the invention. "Therapeutic agents," "drugs," "pharmaceutically active agents," "pharmaceutically active materials," and other related terms may be used interchangeably herein.

Exemplary therapeutic agents for use in conjunction with the present invention include the following: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/ antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/ Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitro- prusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb)

endothelialization facilitators such as VEGF and RGD peptide, and (cc) blood rheology modulators such as pentoxifylline.

A wide range of therapeutic agent loadings can be used in conjunction with the medical devices of the present invention, with the therapeutically effective amount being readily determined by those of ordinary skill in the art. Typical loadings range, for example, from 1 wt % or less to 2 wt % to 5 wt % to 10 wt % to 25 wt % or more of the polymeric mass.

Medical devices having sustained release profiles are beneficial in certain embodiments of the invention. By "sustained release profile" is meant a release profile in which effective amounts of therapeutic agents are released from the medical device to the host tissue or physiological environment over an extended period, such as days, weeks or even months.

Numerous techniques are available for forming polymeric regions in accordance with the present invention. In general, the herein described polymeric regions are processed into a desired form prior to or simultaneously with the formation of covalent crosslinks.

For example, where the polymeric region is formed from one or more materials having thermoplastic characteristics, a variety of standard thermoplastic processing techniques may be used to form the polymeric region. Using these techniques, a polymeric region can be formed, for instance, by (a) first providing a melt that contains polymer(s) or their precursors (e.g., monomers) and any supplemental agents such as catalyst(s), crosslinking agent(s), therapeutic agent(s), and so forth and (b) subsequently cooling the melt. Examples of thermoplastic processing techniques, including compression molding, injection molding, blow molding, spraying, vacuum forming and calendaring, extrusion into sheets, fibers, rods, tubes and other cross-sectional profiles of various lengths, and combinations of these processes. Using these and other thermoplastic processing techniques, entire devices or portions thereof can be made.

Other processing techniques besides thermoplastic processing techniques may also be used to form the polymeric regions of the present invention, including solvent-based techniques. Using these techniques, a polymeric region can be formed, for instance, by (a) first providing a solution or dispersion that contains polymer(s) or their precursors (e.g., monomers) and any supplemental agents such as catalyst(s), crosslinking agent(s), therapeutic agent(s), and so forth and (b) subsequently removing the solvent. The solvent that is ultimately selected will contain one or more solvent species, which are generally selected based on their ability to dissolve the polymer(s) that form the polymeric region (and in many embodiments the therapeutic agent(s) and supplemental agent, if any(s) as well), in addition to other factors, including drying rate, surface tension, etc. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a solution (where solvent-based processing is employed) or a melt (where thermoplastic processing is employed) is applied to a substrate to form a polymeric region. For example, the substrate can correspond to all or a portion of an implantable or insertable medical device to which a polymeric coating is applied, for example, by spraying, extrusion, and so forth. The substrate can also be, for example, a template, such as a mold, from which the polymeric region is removed after solidification. In a specific example, a load bearing joint is cast in this manner.

In other embodiments, for example, extrusion and co-extrusion techniques, one or more polymeric regions are formed without the aid of a substrate. In a specific example, an entire medical device is extruded. In another, a polymeric coating layer is co-extruded along with and underlying medical device body.

Crosslinking may be induced, for example, subsequent to such processes (e.g., by exposure to energy (e.g., heat, radiation, etc.), to a chemical species (e.g., moisture), or to any other agent that results in crosslinking). Crosslinking may also be induced during the forming process in which case these processes are "reactive" processes. A common example is reactive extrusion, in which a material is thermally cured concurrently with extrusion, among other examples.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising a covalently crosslinked polymeric region that comprises at least one block copolymer, said block copolymer comprising a low Tg poly(fluorocarbon) block and a high Tg block selected from poly(vinyl aromatic), polyacrylate, and polymethacrylate blocks.

2. The medical device of claim 1, comprising a plurality of crosslinked polymeric regions.

3. The medical device of claim 1, wherein said block copolymer is a multiarm block copolymer comprising a low Tg midblock and a plurality of high Tg end blocks.

4. The medical device of claim 3, wherein said high Tg endblocks are poly(vinyl aromatic) blocks.

5. The medical device of claim 4, wherein said polyvinyl aromatic blocks comprise an aromatic monomer selected from styrene, styrene sulfonic acids and salts thereof, hydroxy styrenes, alkyl substituted styrenes, ether substituted styrenes, ester substituted styrenes, amino substituted styrenes, silyl substituted styrenes, chloromethyl styrenes, allyl substituted styrenes, vinyl pyridines, alkyl substituted vinyl pyridines, and combinations of the same.

6. The medical device of claim 1, wherein molecules of said block copolymer are covalently crosslinked to themselves, to a supplemental polymer, or both.

7. The medical device of claim 6, wherein carbon atoms of said molecules of said block copolymer are covalently bonded to one another.

8. The medical device of claim 6, wherein molecules of said block copolymer are covalently crosslinked to themselves through a multifunctional crosslinking agent.

9. The medical device of claim 8, wherein said multifunctional crosslinking agent comprises reactive groups selected from unsaturated groups, amine groups, carboxyl groups, hydroxyl groups, thiol groups and combinations thereof.

10. The medical device of claim 6, wherein said block copolymer is crosslinked through one or more reactive groups positioned along its length, at its ends, or both.

11. The medical device of claim 10, wherein said reactive groups are selected from silyl groups, anhydride groups, chloromethyl groups, epoxy groups, and combinations of the same.

12. The medical device of claim 10, wherein said reactive groups are alkoxysilyl groups and wherein said polymeric region is crosslinked upon exposure to moisture.

13. The medical device of claim 10, wherein said reactive groups are anhydride groups or chloromethyl groups and wherein said polymeric region is crosslinked via a multifunctional crosslinking agent comprising reactive species selected from amine groups, hydroxyl groups and combinations thereof.

14. The medical device of claim 6, wherein said block copolymer is crosslinked by exposure to a curing agent selected from energy, chemical agents, and combinations thereof.

15. The medical device of claim 1, wherein said covalently crosslinked polymeric region comprises a covalently crosslinked supplemental polymer.

16. The medical device of claim 15, wherein molecules of said supplemental polymer are covalently crosslinked to themselves, to said block copolymer, or both.

17. The medical device of claim 6, wherein said block copolymer is crosslinked by copolymerization of a macromonomer and a monomer, wherein one of said macromonomer and said monomer is a multifunctional monomer.

18. The medical device of claim 17, wherein said block copolymer is crosslinked by copolymerization of a macromonomer having multiple unsaturated groups and a comonomer having a single unsaturated group.

19. The medical device of claim 17, wherein said block copolymer is crosslinked by copolymerization of a macromonomer having a single unsaturated group and a comonomer having multiple unsaturated groups.

20. The medical device of claim 1, wherein said polymeric region corresponds to an entire medical device or to an entire component of a medical device.

21. The medical device of claim 1, wherein said polymeric region is in the form of a layer that at least partially covers an underlying substrate.

22. The medical device of claim 1, wherein a therapeutic agent is provided on, within or beneath said polymeric region.

23. The medical device of claim 22, wherein said therapeutic agent is selected from antiproliferative agents, vascular cell growth promoters, antimicrobial agents, analgesic agents, immune-suppression agents, antiinflammatory agents, antispasmodic agents, alpha blockers, calcium channel blockers, beta agonists, neoplatic agents, cytostatic agents, and combinations thereof.

24. The medical device of claim 1, wherein said medical device is selected from joint prostheses and devices that transit tissue.

25. The medical device of claim 1, wherein said medical device is selected from knee joints, hip joints, spinal disks and nuclei, vascular grafts, artificial ligaments, and belly bands.

26. The medical device of claim 24, wherein said device that transits tissue is selected from needles, sutures, guidewires, catheters, balloons, and balloon catheters.

27. The medical device of claim 1, wherein said poly(fluorocarbon) block comprises a fluorocarbon monomer selected from vinylidene fluoride, hexafluoropropylene, and combinations thereof.

28. A medical device comprising a covalently crosslinked polymeric region that comprises at least one block copolymer, said block copolymer comprising a low Tg block selected from polyalkene, poly(fluorocarbon), polyacrylate and polysiloxane blocks and a poly(vinyl aromatic) high Tg block comprising an aromatic monomer selected from chloromethyl styrenes, allyl substituted styrenes, and combinations of the same.

* * * * *